United States Patent [19]

Curtis et al.

[11] 4,390,499
[45] Jun. 28, 1983

[54] CHEMICAL ANALYSIS SYSTEM INCLUDING A TEST PACKAGE AND ROTOR COMBINATION

[75] Inventors: Huntington W. Curtis, Chelsea, N.Y.; Robert M. Kellogg, Washington Crossing, Pa.; Kerry W. Kissinger, Pennington, N.J.; Robert P. Mappes, Cranbury, N.J.; Emery J. Stephans, Plainsboro, N.J.

[73] Assignee: International Business Machines Corporation, Armonk, N.Y.

[21] Appl. No.: 292,384

[22] Filed: Aug. 13, 1981

[51] Int. Cl.³ .................. G01N 21/07; G01N 35/00
[52] U.S. Cl. .................................. 422/72; 422/61; 422/63; 422/64; 422/102; 422/104
[58] Field of Search .................. 422/63, 61, 64, 72, 422/65, 102, 104

[56] References Cited

U.S. PATENT DOCUMENTS

| | | | |
|---|---|---|---|
| 3,476,515 | 4/1966 | Johnson et al. | 23/230 |
| 3,477,821 | 12/1967 | Hamilton | 23/253 |
| 3,497,320 | 12/1966 | Blackburn et al. | 23/230 |
| 3,532,470 | 1/1968 | Rochte | 23/253 |
| 3,540,857 | 1/1968 | Martin | 23/292 |
| 3,540,858 | 1/1968 | Brown et al. | 23/292 |
| 3,547,547 | 3/1969 | Anderson | 356/197 |
| 3,555,284 | 1/1968 | Anderson | 250/218 |
| 3,582,218 | 10/1969 | Anderson | 356/197 |
| 3,586,484 | 5/1969 | Anderson | 23/230 |
| 3,759,666 | 12/1971 | Hill, Jr. | 23/230 B |
| 3,856,470 | 1/1973 | Cullis et al. | 23/253 |
| 4,065,263 | 12/1977 | Woodbridge | 422/57 |
| 4,119,407 | 10/1978 | Goldstein et al. | 422/72 X |
| 4,135,883 | 8/1977 | McNeil et al. | 422/72 |
| 4,225,558 | 9/1980 | Peterson et al. | 422/72 |
| 4,237,234 | 12/1980 | Meunier | 422/72 X |

Primary Examiner—Michael S. Marcus
Attorney, Agent, or Firm—Thomas J. Kilgannon

[57] ABSTRACT

Apparatus for carrying out in situ chemical analysis of biological fluids is disclosed. A test package adapted for use with spinning rotor includes a sample-compartment, an integral cuvette and compartments for prepackaged reagents. The latter are adapted to be introduced via breakable seals into the sample compartment which contains the sample to be analyzed. The sample and reagents are then introduced via another breakable seal into a cuvette. Under pneumatic and rotational forces, mixing and measuring are carried out in situ. The rotor includes a programmable pressure applying arrangement whereby the dispensing of reagents and the movement of the latter and sample into a cuvette are controlled. Optical measurements are then carried out in situ.

8 Claims, 6 Drawing Figures

U.S. Patent Jun. 28, 1983 Sheet 1 of 3 4,390,499
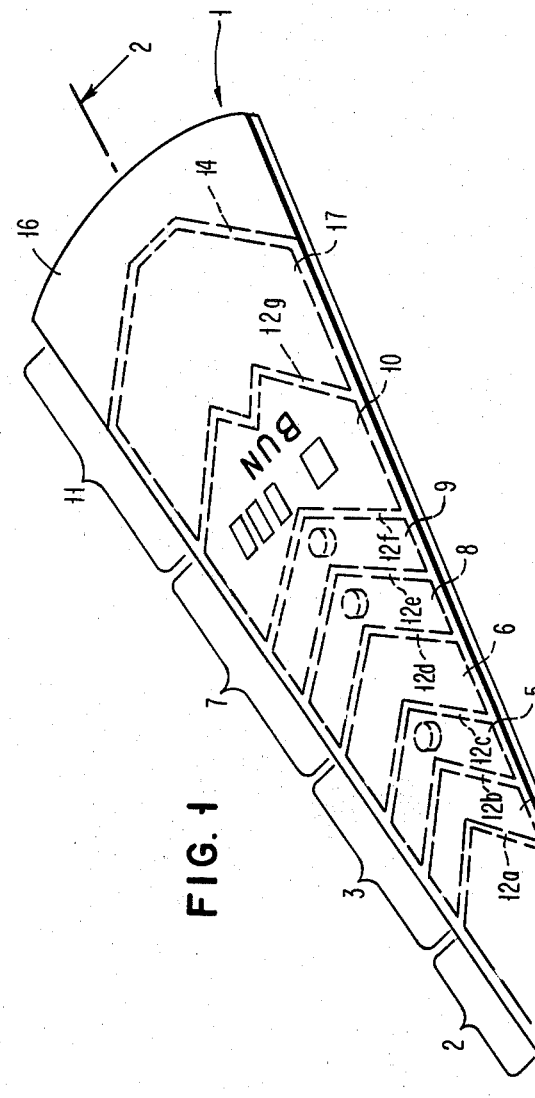
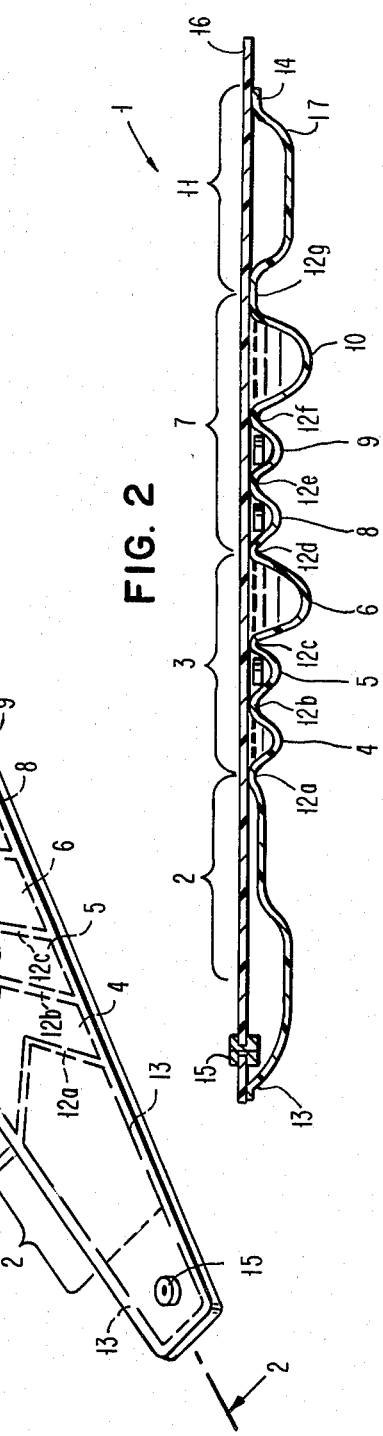

FIG. 4.1
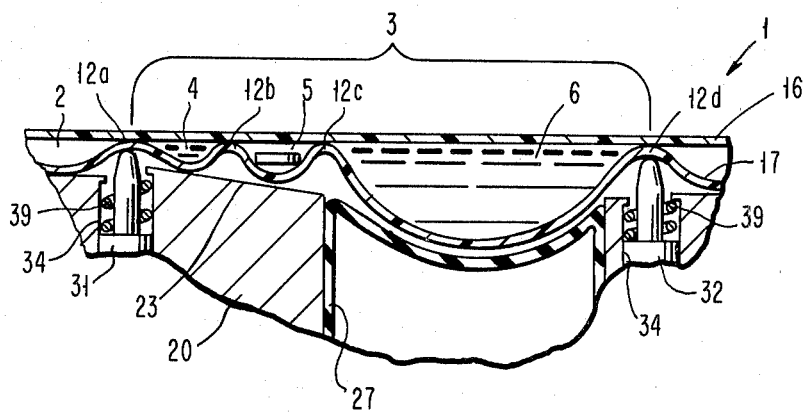
FIG. 4.2
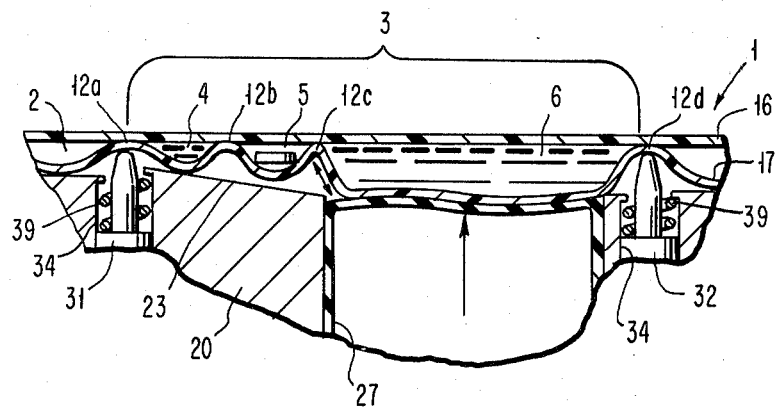
FIG. 4.3
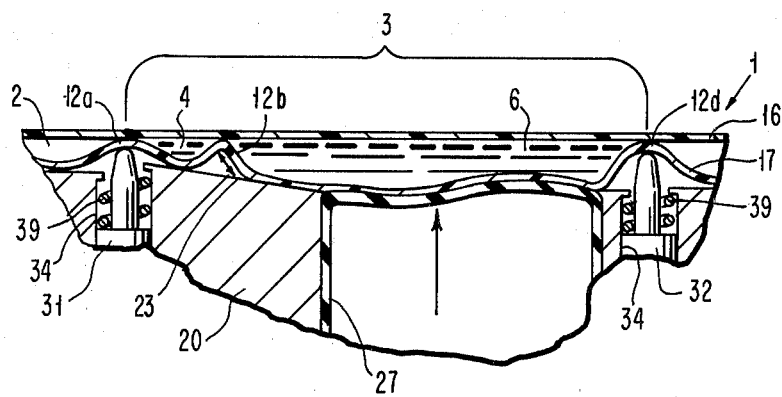

CHEMICAL ANALYSIS SYSTEM INCLUDING A TEST PACKAGE AND ROTOR COMBINATION

DESCRIPTION

1. Technical Field

This invention relates to chemical analysis apparatus and more particularly relates to chemical analysis apparatus utilized in the analysis of biological fluids such as blood. Still more particularly it relates to chemical analysis systems which utilize an integral sample chamber, prepackaged reagent storage chambers and an integral cuvette which are isolated from each other by seals. The test package is designed to mate with recessed chambers in a rotor which contains pressure means for interconnecting the chambers and cuvette. A sample is introduced, into a sample chamber; mixed with reagents; introduced into a cuvette and photometric chemical analysis is carried out in situ while the rotor spins.

BACKGROUND ART

A large body of prior art exists which teaches methods and apparatus for carrying out the chemical analysis of biological fluids. Some of the prior art utilizes test packages which contain prepackaged reagents isolated from a sample chamber by seals. These packages are utilized in an environment wherein the steps of the process are carried out serially in time as each package is moved from one station to another in an enclosed chemical analysis system. Other prior art utilizes test packages without integral cuvettes in a similar serial chemical analysis system. Still other prior art utilizes spinning rotors which act in combination with test packages and utilizes centrifugal force to open reagent packages into a chamber which is a combined mixing chamber-cuvette. Still other rotary systems utilize disposable trays and carry out in situ chemical analysis. Exemplary prior art is as follows:

U.S. Pat. No. 3,532,470 shows a sample holder having a chamber adapted to hold a sample. The holder can be centrifuged to separate serum from blood. After separation, the sample is transferred to a mixing chamber where prepackaged reagents are introduced. This arrangement has no cuvette per se and analysis is not carried out in situ in a rotor arrangement. Thus, while the package structure is very similar to that of the present application, the combination of a test package with prepackaged reagents, a cuvette and a rotor are neither taught nor suggested.

U.S. Pat. No. 3,476,515 shows a flexible test package having an envelope-like configuration wherein selected pods containing reagent may be protected from breaking while other selected pods may have their seals broken by applying pressure to the remainder of the bag. Then, by the application and release of a force on the liquid, the reagents and sample are thoroughly mixed. The shape of the test pack of this patent is totally different and, on the shelf, contains no preformed cuvette chamber. In addition, the patent does not suggest that the test package disclosed can be used in a rotary environment.

U.S. Pat. No. 3,477,821 shows a package which includes an integral cuvette and prepackaged reagents. The package is not adapted for use with a rotor which, upon rotation, permits mixing of a sample and a reagent prior to it being introduced in to cuvette. In the reference, mixing is accomplished by a magnetic stirrer in the cuvette. There is no showing of the combination of a test package with prepackaged reagents and a rotor which carries out mixing and measuring in situ.

U.S. Pat. No. 3,497,320 shows a package wherein prepackaged reagents are disposed alongside a mixing chamber-cuvette. The test package of the reference, while accomplishing the same end result, does not use rotating means to carry out its method. The present invention can be distinguished over this reference on the basis that the combination of the particular test pack with a rotor has not been taught. U.S. Pat. No. 3,540,857 shows a sample holder which has a chamber to which pressure may be applied to force a sample through a filter to another chamber. This holder has no cuvette nor does it have prepackaged reagents.

U.S. Pat. No. 3,540,858 shows a sample holder which has a chamber to which pressure is applied to force a sample through a filter to another chamber. This holder has no cuvette as can be seen from the fact that for optical density testing, the sample with reagent is removed from the holder and pumped into the cell of an analyzer. The patent shows the sample holders arranged in a circle and disposed on a turntable.

U.S. Pat. No. 3,547,547 shows a type of loading disk which, while it has an integral cuvette, does not use prepackaged reagents.

U.S. Pat. No. 3,555,284 shows a transfer disk which does not include prepackaged reagents or an integral cuvette.

U.S. Pat. No. 3,582,218 shows a disposable plastic cuvette into which samples and reagents are transferred by centrifugal force. The samples and reagents are not prepackaged but are introduced sequentially into a holding chamber. All the samples and reagents are first transferred to a cuvette where mixing takes place.

U.S. Pat. No. 3,586,484 shows a transfer disk which does not have an integral cuvette or prepackaged reagents.

U.S. Pat. No. 3,759,666 shows a rotatable loading disk wherein the absorbances of a liquid sample and a reference sample are intercompared. The system includes a series of cuvettes arranged around the periphery of a rotor so that when it is spun, centrifugal force simultaneously mixes and transfers reagents and sample to the cuvettes where an analysis is made spectrophotometrically. The loading disk contains rows of cavities arranged concentrically. Samples to be analyzed are placed in the inner cavities and reagents are placed in cavities at greater radial distance than those containing the serum samples. The disk is then indexed and positioned in the rotor and, as the rotor is spun, centrifugal force moves the sample to the cavity containing the reagent, where they are mixed. The resulting mixture is then moved through a communicating passage to a cuvette where measurements are carried out. In this reference, there are no prepackaged reagents and the cuvettes are not integral with the specimen and the reagent package. The specimen and reagents must be introduced into the disk prior to loading. Also, since the cuvettes of the reference appear to be integral with the rotor, cleaning of the cuvettes is required after each measurement. This reference shows no prepackaged reagent test pack with integral cuvette.

U.S. Pat. No. 3,856,470 shows a transfer disk for individually storing the various constituents of one or more independent reactions and a cuvette rotor. This reference shows no prepackaged reagents and includes cuvettes which are not integral with the disk which holds the sample and reagents.

U.S. Pat. No. 4,135,883 shows a microprocessor controlled centrifuge having a group of cuvettes therein. The apparatus also includes a microdiluter. The cuvettes have hollow main bodies made of transparent material to allow analysis of the specimen therein by a spectrophotometer which reads the cuvettes while rotating. Bags of reagent are received within the cuvettes and are designed to burst under centrifugal force. This permits reagent to flow from the bags into a test chamber within the cuvette's main body.

This reference broadly shows all the elements of an analytical chemistry system. The combination of the present application differs from the reference in that the present test pack does not require centrifugal force to break reagent bags but uses mechanical pressure applied selectively to introduce a reagent and low speed rotation to accomplish mixing. Also, the test pack of the reference is rigid and must be loaded with burstable bags of reagent while the test pack of the present disclosure includes reagent portions, mixing chamber and cuvette in an integral package which is totally disposable. In addition, the combination of the present disclosure does not require high centrifugal speeds permitting a simple and less expensive mechanical arrangement.

From all the foregoing, it should be clear that though the cited prior art is very significant, none of the above cited references appreciate that the combination of the test package and rotor of the present invention could provide a compact, inexpensive way for carrying out in situ clinical analysis of biological fluids.

It is, therefore an object of the present invention to provide a chemical anaylsis system in which a test package and rotor combination permit in situ chemical analysis to be carried out.

Another object is to provide a test package having an integral sample chamber, integral, prepackaged reagent chambers and an integral cuvette.

Another object is to provide a test package which is completely disposable and inexpensive.

Still another object is to provide a rotational chemical analysis system which does not require high speed rotation.

Yet another object is to provide a chemical analysis system which is capable of providing batch testing at higher throughput rates than known prior art systems.

BRIEF SUMMARY OF THE INVENTION

The present invention relates to apparatus for carrying out in situ chemical analysis of biological fluids. Still more particularly, the present invention relates to a test pack adapted for use with a spinning rotor. The test package includes an integral cuvette and compartments for prepackaged reagents. The latter are adapted to be introduced via breakable seals into a chamber which contains a sample which is to be analyzed. The sample and reagents are then introduced via another breakable seal into a cuvette. Under pneumatic and rotational forces, mixing and measuring are carried out in situ. The rotor includes a programmable pressure applying arrangement whereby the dispensing of reagents and the movement of the latter and sample into a cuvette are controlled. Optical measurements are then carried out in situ.

These and other objects, features and advantages will become more apparent from the following more particular description of the preferred embodiments.

BRIEF DESCRIPTION OF THE DRAWINGS

FIG. 1 is a perspective view of the test package showing four major compartments, two of which are further subdivided. The first of the compartments is adapted to carry a sample which is to be subjected to clinical analysis; the second and third compartments are designed to carry reagents in solid and liquid form and both are subdivided to segregate reagents components during storage and the fourth compartment is designed as an optical path compartment which can be subjected to absorption spectrophotometry.

FIG. 2 is a cross-sectional view taken along lines 2—2 of FIG. 1 which shows the relationship of the various compartments to one another.

FIGS. 4.1–4.3 show cross-sectional views of a test package reagent compartment and the pneumatically actuated barriers and diaphragm of the partially cutaway rotor cooperating to mix the desired reagent components.

DESCRIPTION OF A PREFERRED EMBODIMENT

Figure 3:
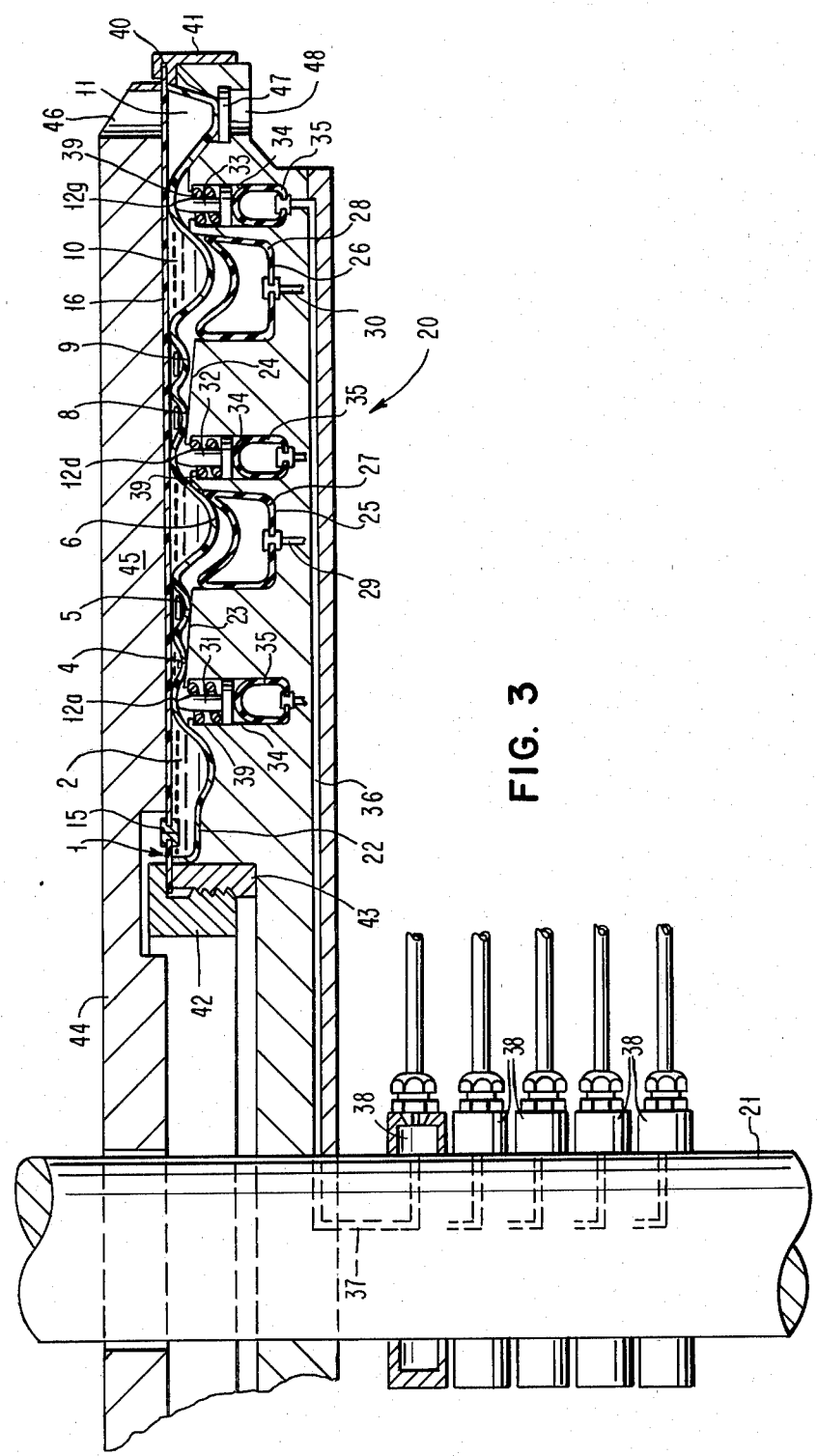
FIG. 3 shows a cross-sectional view of the test package of FIG. 1 already loaded with a sample and diluent disposed in a rotor which is adapted to carry a plurality of such test packages. The rotor which is circular is shown in partial cross-section. Also shown are a plurality of pneumatically actuated barriers and flexible diaphragms the operation of which in a programmed sequence transfers the sample from one compartment to another ultimately providing a sample mixed with various reagents at the optical path compartment. An optical measuring arrangement is also shown disposed in juxtaposition with the optical path compartment.

Referring now to FIG. 1, there is shown therein a perspective view of the test package of the present invention showing four major compartments, two of which are further subdivided. The first of the compartments is adapted to carry a sample which is to be subjected to clinical analysis; second and third compartments are designed to carry reagents in solid or liquid form and both are subdivided to segregate reagent components during storage, and the fourth compartment is designed as an optical path compartment which can be subjected to absorption spectrophotometry.

Before considering FIG. 1 in detail, it should be appreciated that the test package-rotor combination of the present invention is used in the performance of routine clinical chemistry tests for blood serum components, exclusive of electrolytes and blood gases, for example. Some examples of these routine test types are AST (SGOT), Albumin, Alkaline Phosphatase, Amylase, Bilirubin (direct and total), Blood Urea Nitrogen, Cholesterol, CPK, Creatinine, Glucose, SGPT, LDH, Total Protein, Triglycerides, and Uric Acid.

Many chemical analysis approaches exist for determining the concentration of each serum component. For any one component, the methods may vary widely in complexity, expense, performance time, sensitivity, specificity, accuracy and precision (co-efficient of variance). The apparatus to be described in what follows provides an approach for packaging and employing reagents in a way which accommodates a considerable variety of approaches enabling the parallel processing of many different tests on separate measured portions of serum from a single source or from different sources.

The test package to be described is consistent with a known chemical analysis approach which consists of mixing a first reagent with a measured volume of a serum sample and diluent; incubating the serum and diluent for a given time period; mixing the incubated solution with a second reagent and, making a timed measurement of light absorbance in a spectrophotometer which provides an input necessary for the determination of the desired blood serum component.

It should be further appreciated that the reagents used in most analytical chemistry approaches are themselves composed of many separate chemical components. In many instances, some of the components will deteriorate unless stored separately and combined within a few hours of their ultimate use. The present package takes this fact into consideration.

Referring now to FIG. 1 in more detail, test package 1 is shown in a perspective view and, in the preferred embodiment, is divided into four major compartments. The first of these compartments is sample compartment 2 which is adapted to receive a sample such as blood serum upon which measurements are to be made after adding appropriate reagents. Some of these reagents are stored in first reagent compartment 3 which is further subdivided into liquid reagent subcompartment 4, solid reagent subcompartment 5 and liquid reagent subcompartment 6. To the extent that the subcompartments have been characterized as solid or liquid reagent subcompartments for purposes of exemplification, it should be appreciated that subcompartments 4,5 could just as easily have their contents interchanged. Another major compartment is second reagent compartment 7 which like compartment 3 is further subdivided into solid reagent subcompartment 8, solid reagent subcompartment 9 and liquid reagent subcompartment 10. The last of the major compartments is optical path compartment or cuvette 11.

The various compartments and subcompartments are isolated one from the other by rupturable seals 12a–12g. Another seal 13 which is not subject to rupture extends along the edges of test package 1 while nonrupturable seal 14 forms the terminal end of cuvette 11. A resealable aperture or port 15 which is utilized for introducing the blood serum sample into sample compartment 2 is shown disposed in upper element 16 of test package 1. While not specifically shown in FIG. 1, it should be appreciated that test package 1 additionally includes a pliable element 17 which is sealed to element 16 by means of nonrupturable seals 13,14.

The structure of test package 1 can be clearly understood from a consideration of FIG. 2 in conjunction with FIG. 1. FIG. 2 is a cross-sectional view taken along line 2—2 of FIG. 1 which shows the relationship of the various compartments to one another and how upper element 16 is sealed to a pliable element 17 to form the various compartments. In FIG. 2, pliable element 17 is shown in sealed relationship with upper element 16 by means of rupturable seals 12a–12g and nonrupturable seals 13,14. FIG. 2 clearly shows the compartmentalized nature of test pack 1 with major compartments 2, 3, 7, 11 being formed by sealing portions of pliable element 17 to upper element 16. Closer inspection of FIG. 2 shows a liquid reagent disposed in subcompartment 4, a solid reagent in the form of a pill in subcompartment 5 and another liquid reagent disposed in subcompartment 6. Also, subcompartments 8,9 are shown containing solid reagents while subcompartment 10 is shown containing another liquid reagent. Upper element 16 is a flat, rigid, somewhat brittle polymeric slab or sheet to which pliable element 17 is bonded. Pliable element 1 maybe made of flexible polymeric material. Both upper element 16 and pliable element 17 must allow transmission of visible and near ultraviolet light so that, given a reproducible path length in a liquid contained in cuvette 11, the absorption of light at a selected wavelength may be quantitatively determined.

Two types of bonding are employed in fabricating test package 1 shown in FIGS. 1,2. Nonrupturable seals 13,14 are permanent seals attaching portions of pliable element 17 to portions of upper element 16. The other type of bonding employs rupturable seals 12a–12g which are temporary, force-sensitive adhesive lines or zones bonded to portions of upper element 16 which can be sequentially released by combinations of hydraulic, pneumatic and centrifugal forces. The rupturable seals 12a–12g are maintained during the entire pre-use storage period of each test package 1 and are unaffected by normal handling. In addition, each package is marked with the identity of the test for which it is designed in both user and machine readable forms. These markings are positioned as shown in FIG. 1 over subcompartment 10, for example, where they will not interfere with measurements requiring the materials to be transparent.

In FIG. 1, test package 1 has a length of approximately 9 centimeters. Table I below shows the approximate volumes which the various compartments and subcompartments can contain before temporary seals 12a–12g are ruptured.

TABLE I

| COMPARTMENTS OR SUBCOMPARTMENTS | VOLUME |
| --- | --- |
| 2 | 0.7 ml |
| 4 | 0.1 ml |
| 5 | 0.1 ml |
| 6 | 1.0 ml |
| 8 | 0.1 ml |
| 9 | 0.1 ml |
| 10 | 1.0 ml |
| 11 | 2.5 ml |

FIG. 3 shows a cross-sectional view of the test package of FIG. 1 already loaded with a sample and diluent disposed in a rotor which is adapted to carry a plurality of such test packages. The rotor which is circular is shown in partial cross-section. Also shown are a plurality of pneumatically actuated barriers and flexible diaphragms. The operation of these barriers and diaphragms in a programmed sequence transfers the sample from one compartment to another ultimately providing a sample mixed with various reagents at the optical path compartment or cuvette. An optical measuring arrangement is also shown in juxtaposition with the cuvette.

Prior to discussing FIG. 3 in detail, it should be understood that appropriately designed apparatus exists for furnishing the necessary functions external to test pack 1. This apparatus includes apparatus for introducing serum and diluent into sample compartment 2 and a chamber for bringing the test package and its contents to a desired reaction temperature (e.g., 37° C.). To the extent that these features are well known in other chemical analysis apparatus and form no part of the present invention, let it suffice to say that test pack 1 and the rotor shown in FIG. 3 may be enclosed in an appropriately temperature controlled environment.

As will be seen in connection with the discussion of FIG. 3, the steps of mixing together the component parts of first reagent compartment 3 and similarly mixing the reagent components of second reagent compartment 7; initiating the mixing and reacting of the serum and reagents from first reagent compartment 3; timing this reaction and then initiating the further mixing of the resulting reaction mixture with the reagent of second reagent compartment 7 and, finally causing the resulting mixture to flow into cuvette 11 where it will be measured spectrophotometrically as a function of time can be carried out using the apparatus shown in FIG. 3.

Referring now to FIG. 3 in detail, a single test package 1 already loaded with serum and diluent in sample compartment 2 is shown in cross-section disposed in an appropriately formed rotor 20 which is shown in a partially cut-away, cross-sectional view and is fastened to a drive shaft 21. The latter is driven by a motor (not shown) at a speed of approximately 200 rpm. Rotor 20 is designed to carry a plurality of test packages at the same time. In one arrangement, each test package 1 fits within a ten degree angle of the rotor. Thus, rotor 20 may carry thirty-six test packages 1 and carry out measurements on them at the same time. In FIG. 3, sample compartment 2 is receivable in a shaped recessed 22 in rotor 20 and subcompartments 4,5 rest on a ramp-like surface 23 of rotor 20. Similarly, subcompartments 8,9 rest on a second ramp-like surface 24 of rotor 20. Subcompartments 6,10 extend into recesses 25,26, respectively formed in rotor 20. Recesses 25,26 have receivable therein diaphragms 27,28, respectively, which are pneumatically actuated by means of tubes 29,30. Tubes 29,30 are connected to circular galleries (not shown) which are, in turn, connected via separate tubes to separately controlled sources of pressure such that when pressure is applied to such a tube, all diaphragms 27, for example, connected to the same circular gallery expand at the same time. Similarly, when pressure is applied via a tube to a gallery to which tube 30 is connected, all diaphragms 28 connected to that gallery expand at the same time. In this way, pressure can be applied to subcompartments 6,10 at different times to cause the rupture of selected ones of rupturable seals 12a–12g.

Since it is desired to mix the reagent component in the various subcompartments and then mix the resulting reagent substantially with the sample in sample compartment 2, first reagent compartment 3 and second reagent compartment 7 must be isolated from each other and from sample compartment 2 and cuvette 11. Isolation is achieved by means of pneumatically actuated barriers 31,32 and 33 which initially press against rupturable seals 12a,12d and 12g, respectively. Barriers 31–33 are disposed within recesses 34 in rotor 20; the bottom portions of which carry diaphragms 35. Each of diaphragms 35 is connected by a separate tube 36 (only one of which shown in FIG. 3 connected to the rightmost diaphragm 35) which is connected to a tube 37 in shaft 21. Tube 37 is connected to an annular plenum chamber 38 within which shaft 21 rotates. Tube 36 is connected to a circular gallery which applies a pressure via diaphragm 35 to each barrier 33 disposed at the same radial position and associated with its own test pack 1.

Thus, when pressure is applied to plenum chamber 38, via tubes 37,36, thirty-six barriers 33 are actuated against thirty-six rupturable seals 12g. In a similar way, barriers 31,32 can be simultaneously or separately actuated. When diaphragms 35 are inflated, barriers 31 are urged against retention springs 39 which are, in turn, held against lips extending plurality across recesses 34. From the foregoing, it should be clear that any number of test packs 1 up to thirty-six in number can be processed at the same time using the rotor arrangement of FIG. 3. It should also be clear that plenum chamber 38 and other similar chambers 38 in FIG. 3 can be programmed by means of actuable valves (not shown) to cause the actuation of diaphragms 27,28 and diaphragms 35 in a preprogrammed manner.

In FIG. 3, the extremities of test pack 1 are clamped to rotor 20. Test pack 1 is clamped at its rightmost extremity by inserting a portion of upper element 16 in a slot 40 in an element 41 which is rigidly connected to rotor 20 and at its leftmost extremity by inserting a portion of element 16 into a space formed between a ring nut 42 and a threaded ring 43. In this manner, test package 1 is rigidly held during rotation of rotor 20. A cover plate 44 includes a portion 45 which rests on the surface of upper element 16 securing test package 1 firmly in place during rotation while simultaneously acting as a surface against which barriers 31–33 press to isolate the major compartments. Cover plate 44 includes an aperture 46 which is in registry with cuvette 11, a quartz plate 47 and another aperture 48. Quartz plate 47 is positioned in rotor 20 so that monochromatic light passes from a source (not shown) via aperture 46, cuvette 11 and aperture 48. A photomultiplier tube (not shown) is disposed beneath aperture 48. As shown in FIG. 3, quartz plate or window 47 in rotor 20 is spaced from the surface of upper element 16 by a fixed distance, e.g. 1 cm, so that monochromatic light will encounter the same path length as it passes through the cuvette 11 of each test pack 1. As each test pack 1 during the revolution of rotor 20 sweeps past the position of the monochromatic beam, the absorbance of the liquid held in cuvette 11 is measured by a photomultiplier tube in a manner well known to those skilled in such measuring arts.

Referring now to FIGS. 4.1–4.3, there is shown therein cross-sectional views of first reagent compartment 3, diaphragm 27 and pneumatically actuated barriers 31,32. The relative positions of these elements are shown when it is desired to cause breakage of rupturable seals 12b,12c to achieve mixing of liquid reagent from subcompartment 6 with solid and liquid reagents from subcompartments 5,4, respectively. FIGS. 4.1–4.3 show the sequence for constituting the components in subcompartments 4, 5, 6 into a first reagent which is to be mixed with serum in compartment 2. In FIG. 4.1, pneumatically actuated valves 31,32 are in their actuated state while diaphragm 27 has no pressure applied to it. Barriers 31,32 are positioned beneath rupturable seals 12a,12d, respectively, and, in this manner, hold upper element 16 against cover plate portion 45. With barriers 31,32 in their actuated state, a valve supplying pressure to diaphragm 27 is actuated forcing the upper portion of diaphragm 27 against the bottom of subcompartment 6. Because the action being described is carried out while rotor 20 is spinning, the combination of centrifugal force due to the spinning rotor and the force applied by diaphragm 27 causes tension in the pliable element 17 side of test package 1.

Since pneumatically actuated barrier 32 and portions of nonrupturable seals 13 of the test package prevent separation between upper element 16 and pliable element 17 at these points, tension at rupturable seal 12c is sufficiently high (as shown by the double ended arrow in FIG. 4.2) to cause it to rupture. Continued application of force by diaphragm 27 as shown in FIG. 4.3 increases tension in rupturable seal 12b (as shown by a double ended arrow in FIG. 4.3) so that rupturable seal 12b also opens. Once rupturable seal 12b ruptures, sub-compartments 4, 5, 6 are reduced to a single compartment. Now, by releasing pressure on diaphragm 27 through its associated tubes and control valves, centrifugal force moves all solids and liquids contained in this single chamber toward barrier 32. By again pressurizing diaphragm 27, the reagents are forced toward barrier 31. By repeating this process a number of times, solid reagents may be dissolved and thoroughly mixed with the other components. In a similar way, diaphragm 28 may be actuated to rupture rupturable seals 12e,12f while second reagent compartment 7 is held by barriers 32,33 at rupturable seals 12d,12g, respectively.

Referring again to the apparatus shown in FIG. 3 which can be programmed to provide a number of possible sequences, the following eight minute analysis cycle is representative of a method for analysis of various blood serum components. When a particular test is desired, the correspondingly labeled test package 1 containing desired reagent components is removed from refrigerated storage. Precise amounts of serum and diluent with quantities appropriate to the particular test are then injected via aperture 15 into sample compartment 2. After placement in rotor 20 together with any other test packages which one may desire to run simultaneously, rotor 20 is brought up to operating speed and the reagents in subcompartments 4, 5, 6 and the reagents in subcompartments 8, 9, 10 are separately mixed in the manner described hereinabove in connection with FIGS. 4.1-4.3. A period of one minute, during which the package temperature is brought to approximately 37° C., is allocated for the reagent preparation phase. Under timer control, to accomplish mixing during this one minute period, barriers 31-33 apply forces to package 1 sufficient to prevent flow between sample compartment 2 and first reagent compartment 3, first reagent compartment 3 and second reagent compartment 7, and second reagent compartment 7 and cuvette 11. Diaphragm 27 is then actuated, supplying sufficient force to break rupturable seal 12g followed by the breaking of rupturable seal 12b in a similar manner. At the same time, the actuation of diaphragm 28 breaks rupturable seals 12e and 12f. After approximately two seconds, diaphragms 27,28 are depressurized allowing centrifugal force to move the enclosed liquids to greater radial distances from the center of rotor 20. After two more seconds, diaphragms 27,28 are again activated. This cycle is repeated during a one minute mixing interval with diaphragms 27,28 being depressurized at the end of the interval.

After the passage of one minute, barrier 31 is released and diaphragm 27 is pressurized with sufficient force to break rupturable seal 12a thereby forcing some of the now mixed reagent from first reagent compartment 3 into sample compartment 2. Diaphragm 27 is then depressurized, allowing centrifugal force to drain the contents of compartment 2 toward barrier 32. Repetition of the pressurization and depressurization cycle of diaphragm 27 for one minute insures thorough mixing of the sample and reagent. The first reaction phase lasts for 5.9 minutes, an incubation period sufficient for many chemistries at 37° C. After 6.9 minutes, barrier 32 is released and diaphragm 28 is actuated with sufficient force to break rupturable seal 12d. After two seconds, diaphragm 28 is depressurized and this four second cycle is repeated twice with diaphragm 28 ending in its depressurized state.

Finally, after the passage of 7.1 minutes, pneumatic pressure is applied to barrier 32 and removed from barrier 33. Diaphragm 28 is again actuated, breaking rupturable seal 12g and under centrifugal force, the final reaction mixture is caused to flow into cuvette 11.

As previously discussed, the space between upper element 16 and quartz window 47 in the region of cuvette 11 approximately one centimeter. As the cuvette 11 of each test package 1 is swept past the position of a monochromatic beam, the absorbance of the contained liquid is measured. For end point reactions, several readings spaced in time may be averaged during a measurement period which concludes after the passage of eight minutes. For kinetic reactions successive time-dependent absorbance readings for a particular test package may be determined and from these measurements, the concentration-related slope may be calculated.

Having thus described our invention, what we claim as new, and desire to secure by Letters Patent is:

1. Chemical analysis apparatus comprising in combination a rotor having means adapted to support at least one test package therewithin,
   at least one test package receivable in said rotor comprising:
   a flexible sample compartment for receiving a biological fluid sample therein,
   at least one flexible reagent storage compartment disposed in breakable, sealed relationship with said sample compartment,
   a flexible cuvette disposed in breakable, sealed relationship with said reagent storage compartment,
   said flexible cuvette being positioned outermost in said rotor, and,
   means integral with said rotor for rupturing the breakable, sealed relationship between said sample compartment, said reagent storage compartment and said cuvette.

2. Chemical analysis apparatus according to claim 1 further including means connected to said rotor for spinning said rotor.

3. Chemical analysis apparatus according to claim 1 wherein said at least one test package further includes a transparent element to which said sample compartment, said at least a reagent storage compartment and said cuvette are attached by means of breakable and unbreakable seals.

4. Chemical analysis apparatus according to claim 1 wherein said at least one flexible reagent storage compartment further includes at least one subcompartment disposed in breakable, sealed relationship within said at least one flexible reagent storage compartment.

5. Chemical analysis apparatus according to claim 1 further including means disposed in juxtaposition with said cuvette for sensing an optical characteristic of said sample.

6. Chemical analysis apparatus according to claim 5 wherein said means for sensing includes a quartz window disposed in said rotor positioned in registry with said flexible cuvette.

7. Chemical analysis apparatus according to claim 1 wherein said means for rupturing includes pneumatically actuated barriers disposed in said rotor and positioned between said sample compartment and said at least one flexible reagent storage compartment and, between the latter and said cuvette, and a pneumatically actuated diaphragm disposed in said rotor positioned adjacent to said at least one flexible reagent storage compartment.

8. Chemical analysis apparatus according to claim 7 further including pneumatic means connected to said barriers and said diaphragm for actuating said barriers and said diaphragm separately or simultaneously.

* * * * *

UNITED STATES PATENT AND TRADEMARK OFFICE
CERTIFICATE OF CORRECTION

PATENT NO. :  4,390,499
DATED      :  June 28, 1983
INVENTOR(S):  H.W. Curtis, R.M. Kellogg, K.W. Kissinger, R.P. Mappes and E.J. Stephans It is certified that error appears in the above-identified patent and that said Letters Patent is hereby corrected as shown below:

Column 7, line 46, Delete "substantially" and insert --sequentially--.

Column 10, line 47, Delete "a" and insert --one--.

Signed and Sealed this

Thirteenth Day of August 1985

[SEAL]

Attest:

DONALD J. QUIGG

Attesting Officer    Acting Commissioner of Patents and Trademarks